United States Patent [19]
Dreux

[11] Patent Number: 6,148,661
[45] Date of Patent: Nov. 21, 2000

[54] METHOD OF SEPARATING AND RAPIDLY ANALYZING A SAMPLE

[75] Inventor: Michel Dreux, Olivet, France

[73] Assignees: Sedere S.A., Alfortville; Universite d'Orleans-UFR de Sciences, Orleans, both of France

[21] Appl. No.: 09/211,554

[22] Filed: Dec. 15, 1998

[30] Foreign Application Priority Data

Dec. 22, 1997 [FR] France ................................... 97 16240
Dec. 9, 1998 [FR] France ................................... 98 15518

[51] Int. Cl.[7] .......................... G01N 30/00; B01D 15/08; G01T 1/167
[52] U.S. Cl. .......................... 73/61.52; 210/656; 250/301
[58] Field of Search ................................. 73/61.52, 61.53, 73/61.55, 61.58; 210/656, 198.2, 659; 250/301

[56] References Cited

U.S. PATENT DOCUMENTS 3,920,398   11/1975   Small et al. .......................... 23/230 R

OTHER PUBLICATIONS

Dobson, G. et al.: "Silver Ion Chromatography of Lipids and Fatty Acids" Journal of Chromatography B: Biomedical Applications, vol. 671, No. 1, Sep. 15, 1995, pp. 197–222.

Niemi R. et al.: "Simultaneous Determination of Clodronate and Its Partial Ester Derivatives by Ion–Pair Reversed–Phase High–Performance Liquid Chromatography Coupled With Evaporative Light–Scattering Detection" Journal Of Chromatography B: Biomedical Sciences and Applications, vol. 701, No. 1, Nov. 7, 1997, pp. 97–102.

J. M. Charlesworth: "Evaporative Analyzer as a Mass Detector for Liquid Chromatography" Analytical Chemistry, vol. 50, No. 11, Sep. 1978, pp. 1414–1420.

French Preliminary Search Report dated Sep. 7, 1998.

*Primary Examiner*—Hezron Williams
*Assistant Examiner*—Jay L. Politzer
*Attorney, Agent, or Firm*—Baker & Daniels

[57] ABSTRACT

A method of separating and analyzing slightly volatile cations and/or anions contained in a sample immediately and simultaneously. The sample is injected into a chromatography device in liquid phase co-operating with at least one stationary phase likely to retain the cations and the anions contained in the sample by competing interactions with the stationary phase or phases. The cations and anions are eluted by feeding at least one mobile phase which can be evaporated through the stationary phase or phases. The cations and the anions present in the mobile phase or phases are analyzed with the aid of an evaporative light scattering detector.

13 Claims, 4 Drawing Sheets

METHOD OF SEPARATING AND RAPIDLY ANALYZING A SAMPLE

BACKGROUND OF THE INVENTION

1. Field of the Invention

The present invention relates to a method of separating and analysing slightly volatile cations and anions contained in a sample immediately and simultaneously.

2. Description of the Related Art

Numerous control laboratories, of which laboratories which analyse domestic water can be cited as an example although there are others too, are keen to have simple and rapid methods of analysing samples immediately, without the need for preparations beforehand or adjustments during analysis.

So far, specialists have failed to come up with methods of a nature that will satisfy these various requirements yet produce accurate and comprehensive results.

SUMMARY OF THE INVENTION

The objective of the present invention is to remedy this failure by proposing a method of the type mentioned above, characterised in that: the sample is injected into a chromatography device in liquid phase co-operating with at least one stationary phase likely to retain the cations and anions contained in the sample by competing interactions with the stationary phase or phases; the cations and anions are eluted by feeding at least one mobile phase which can be evaporated through the stationary phase or phases; and the cations and the anions present in this mobile phase or phases are analysed immediately by means of an evaporative light scattering detector (ELSD).

The essential characteristic of the invention is that a specific piece of detection apparatus is used, i.e. a light-diffusion evaporative detector such as the device sold by SEDERE under the trade name SEDEX®, for example.

This device, which is designed for analysing effluent, in particular from chromatography columns, has the advantage of being universal, i.e. it can be used to analyse all non-volatile compounds, particularly mineral and organic cations and anions and can be so without the need to prepare the sample or apply any specific chemical treatment, except possibly to convert volatile compounds into non-volatile compounds.

DETAILED DESCRIPTION OF THE INVENTION

The operating principle of such a device is as follows: the compounds to be analysed are conveyed by a liquid mobile phase which is more volatile then they are, and this is then evaporated at a relatively low temperature (which may be in the order of 40° C.) so that all that remains behind are residual micro-particles which can be detected by light scattering.

The effluents arriving from chromatography columns can then be analysed immediately, the only proviso being that the eluant chosen is sufficiently volatile to be used directly as a mobile phase on a level with the ELSD.

For the purposes of the invention, as a general rule the sample to be analysed is fed through two columns coupled with one another, in particular set up in series and, as required, with a facility for automatic switching so that they can be isolated from one another, one of these columns retaining the cations whilst the other retains the anions, or through one column filled with two different stationary phases, which may optionally be mixed, one of which retains the cations and the other the anions, or alternatively a column filled with a single stationary phase which will retain the cations and the anions.

It has been confirmed that a method of this type allows mixtures of cations and anions to be analysed simultaneously and produces a high degree of sensitivity (several ppm directly).

In accordance with the invention, the stationary phase which retains the cations is a cation exchanger as a general rule.

To this end, there is an advantage to be had from using a strong cation exchanger SCX (Strong Cation Exchanger), i.e. a resin whose active groups are the $SO_3^-$ groups, such as SCX resin sold by WHATMAN under the PARTISIL® trade name, for example. However, it would also be conceivable to use a weak cation exchanger WCX (Weak Cation Exchanger) in which the $SO_3^-$ groups are replaced by $COO^-$ groups. Similarly, silica may be replaced by a polymer base or coated with polymer.

In these resins, the $SO_3^-$ or $COO^-$ groups attract the positively charged ions, i.e. retain the cations.

The stationary phase which retains the anions may in turn be a strong anion exchanger or, as is the case, a weak anion exchanger (SAX or WAX) such as the SAX resin marketed under the name of SHIMADZU IC $A_1$®.

To this end, it has also been possible to use a specific porous graphitized carbon phase (CGP) such as that marketed by HYPERSIL under the name of HYPERCARB®.

It has been established that this stationary phase, the structure and mode of action of which are not accurately understood, exhibits at least as many hydrophobic reactions as conventional non-polar silicas (C18) and, in parallel, electronic interactions, probably consecutive, on the $\pi$ electrons of the graphite structure; consequently, it can be used in the same fields as non-polar silicas would be used and also as a means of retaining polar or even ionic solutes.

It has therefore been verified that, in accordance with the invention, the inorganic anions can be locked on this stationary phase by a simple percolation of water and then unlocked by means of a volatile eluant having only a relatively low ionic strength, which can be used directly as a mobile phase for subsequent analysis by light scattering.

It should also be pointed out that, surprisingly, it was found using the invention that both the cations and the anions could be separated by means of a single stationary phase comprising a functionalised polymer of the "PRPX 200" type, initially devised as a cation exchanger: it was found that on a stationary phase of this type and by selecting an appropriate eluant, the anions can be eluted not together as a dead volume but separately, i.e. with a certain degree of retention and a certain degree of selectivity.

As outlined above, the method proposed by the invention therefore allows the anions and/or the cations contained in a sample to be locked on one or two stationary phases and eluted selectively with a view to detection using the ELSD.

The essential feature of the method proposed by the invention, however, is the fact that it allows anions and cations to be analysed immediately and simultaneously by feeding a mobile phase through the one or two stationary phases to elute the cations or anions followed immediately by a mobile phase to elute the anions or cations or, alternatively, a mobile phase to elute the cations and anions simultaneously in a selective manner, i.e. without any co-elution of the different species.

Applying this method therefore involves choosing identical or compatible mobile phases to elute the anions and the cations and which at the same time are sufficiently volatile for direct use as mobile phases for analysis purposes using the ELSD.

It should be noted that these eluant mobile phases must, in addition, contain ions (anions and cations) which are likely to compete in their interactions with the anions and cations to be analysed at the active sites of the stationary phases.

For the purposes of the invention, it was possible to use mobile phases to elute the cations and mobile phases to elute the anions made up of solutions of different compounds but compatible with the ELSD, i.e. volatile, such as mixtures or otherwise of acids (HCOOH, $CH_3COOH$, $CF_3COOH$) and bases ($NH_4OH$, $Et_3N$, pyridine, ethylene diamine) or volatile salts (carbonates and carbamates of ammonium).

According to one preferred, characteristic of the invention, the mobile phase used to elute the cations and the mobile phase used to elute the anions are preferably solutions of a same composition but having different concentrations of ions but it is also possible to use solutions of different compounds with identical or different concentrations.

Advantageously, it proved possible to use aqueous solutions of formic acid and ammonia for this purpose.

According to another feature of the invention, after injecting the cations and anions to be analysed into the chromatography device, an aqueous solution of formic acid and ammonia in a low concentration is fed through the stationary phase or two stationary phases so that the cations remain locked whilst the anions are eluted, followed by an aqueous solution of formic acid and ammonia at a higher concentration in order to elute the cations.

By way of example, the solution with the weak concentration may contain between 20 and 40 mM/1 of formic acid and between 10 and 30 mM/1 of ammonia and the solution with a high concentration between 80 and 120 mM/1 of formic acid and between 70 and 95 mM/1 of ammonia.

It is essential that the mobile phase with a low concentration is fed through the column(s) first followed by that with the higher concentration in order to ensure that the cations and anions are not eluted simultaneously or in effect only some of them are.

It should be pointed out that by virtue of another characteristic of the invention, it would be conceivable to incorporate one or more stationary phases in the injection loop of the chromatography device in order to produce a pre-concentration which may or may not be selective (cations, anions etc.).

Such pre-concentration systems, which can be used online or offline, can be used to carry out analysis on low concentrations (less than $mg \times l^{-1}$).

It should also be pointed out that the simultaneous elution of cations and anions may also be accompanied in addition by the elution of neutral molecules without modifying the eluents or by adding an organic modifier to them such as those used in chromatography where the polarity of the phases are inverted.

The characteristics of the method proposed by the invention will be described in more detail below with reference to various examples:

EXAMPLE 1

Analysis of Cations on a Cation Exchanger

A mixture of mono-cations (Na, K) and di-cations (Mg, Ca) was analysed on a PARTISIL®SCX 10 µm column (4.6×100 mm). After injecting in this mixture, a mobile phase comprising a solution containing 100 mM/1 of formic acid and 87.6 mM/1 of ammonia was fed through this column at a flow rate of 1 ml/min.

The eluant was analysed with a ELSD at the output of the column.

The chromatogram obtained is illustrated in FIG. 1, in which the first peak corresponding to a retention time of 1.308 min. represents—the anions which are eluted instantly whereas the subsequent peaks corresponding respectively to retention times of 2.31; 2.708; 4.941 and 6.061 min. represent the $Na^+$, $K^+$, $Mg^{++}$ and $Ca^{++}$ ions.

This example demonstrates that a mixture such as this can be analysed by the method proposed by the invention.

EXAMPLE 2

Analysis of Anions on an Anion Exchanger

A mixture of chloride, nitrate and sulphate is analysed on a SHIMADZU IC $A_1$® column (4.6×100 mm).

After injecting in this mixture, a mobile phase comprising a solution containing 10 mM/1 of $CF_3COOH$ was fed through the column at a flow rate of 1 ml/min.

The eluant was then analysed with the ELSD at the output of the column.

The chromatogram obtained is illustrated in FIG. 2, in which the first peak corresponding to a retention time of 1.22 min. represents the cations, which emerge as dead volume whilst the subsequent peaks corresponding respectively to retention times of 3.23; 4.20 and 6.12 min. represent the chlorides, nitrates and sulphates.

This example demonstrates that the method proposed by the invention can also be used to analyse a mixture of this type.

EXAMPLE 3

Analysis of Anions on a Porous Graphitized Carbon Resin

A mineral water (Perrier® water) was analysed on a HYPERCARB® 5 µm column (4.6×100 mm).

After injecting in the water to be analysed, a mobile phase comprising a solution containing 30 mM/1 of formic acid and 20 mM/1 of ammonia was fed through this column at a flow rate of 0.5 ml/min.

The eluant was then analysed on the ELSD at the output of the column.

The chromatogram obtained is illustrated in FIG. 3, in which the first peak corresponding to a retention time of 2.482 min. represents the cations emerging virtually instantaneously whilst the subsequent peaks corresponding to retention times of 3.372; 3.978 and 5.777 min. represent the chlorides, the sulphates and the nitrates.

This example demonstrates that the method proposed by the invention can also be used for this type of analysis.

EXAMPLE 4

Pre-concentration of Anions on a Porous Graphitized Carbon Resin

This example was set up under conditions identical to those used for example 3.

10 ml of solution containing 5 ppm of $SO_4^-$ ions is fed through 200 mg of a HYPERCARB® resin and the concentrate of sulphate anions retained on this resin is unlocked with 1 ml of eluant solution containing formic acid and ammonia; this eluant was then analysed at the output of the column using the ELSD.

The chromatogram obtained is illustrated in FIG. 4A, in which the peak corresponding to a retention time of 3.837 represents the $SO_4^-$ ions, the concentration of which is about 37 ppm.

To provide a comparison, standard solutions of sodium sulphate with concentrations of 30 and 40 ppm of sulphate were analysed under the same conditions as those selected for example 3.

The chromatograms obtained are reproduced in FIGS. 4B and 4C, in which the first peak corresponding to a retention time of 2.233 or 2.25 min. represents the sodium whilst the second peak corresponding to retention times of 3.94 or 3.958 min. represents the sulphate ion.

It should be noted that a pre-concentration of 100% is tantamount to metering 50 ppm of $SO_4^-$ whereas only 37 ppm were obtained, which means that the pre-concentration was 74%.

EXAMPLE 5

Analysis of Anions in the Presence or Absence of the Associated Cations

A standard solution containing 25 ppm of $Na_2SO_4$ was analysed under conditions identical to those selected for example 3.

The chromatogram obtained is illustrated in FIG. 5A, in which the first peak corresponding to a retention time of 2.23 min. represents the sodium whilst the second 30 peak corresponding to a retention time of 4.368 min. represents the sulphate ion.

This analysis was re-initiated after percolating the sample to be analysed through a cation exchanger cartridge beforehand.

The chromatogram obtained is illustrated in FIG. 5B, in which the single peak corresponds to a retention time of 4.205 min. and represents the sulphate ion.

This demonstrates that pairing the HYPERCARB® resin with a cation exchanger makes it possible to get rid of the corresponding sodium peak.

In a situation where the few anions were being analysed, even the very few anions retained could be metered without being hampered by the elution or even the co-elution of cations.

EXAMPLE 6

Simultaneous Analysis of Anions and Cations by Coupling Two Different Stationary Phases Using an Eluant of a Given Composition at Two Different Concentrations Several samples were analysed on two stationary phases made up by combining a PARTISIL SCX® silica similar to that used in example 1 and a HYPERCARB® resin similar to that used in example 3.

After injecting in the sample to be analysed, a first mobile phase made up of a solution containing 30 mM/1 of formic acid and 20 mM/1 of ammonia was fed through the columns for 4 min. (i.e. between the times 0 and 4 min.) at a flow rate of 0.4 ml/min. and then, for the next 16 min. (i.e. between the times 4 and 20 min.) a second mobile phase made up of a solution containing 100 mM/1 of formic acid and 87 mM/1 of ammonia.

The eluant was analysed at the output of the column on the ELSD.

The chromatograms obtained are illustrated in FIGS. 6A, 6B and 6C.

It should be noted that the small intermediate peak between the peaks corresponding to the retention times of 7.358 and 11.858 min. correspond to the low concentration $K^+$ ion.

Figure 1:
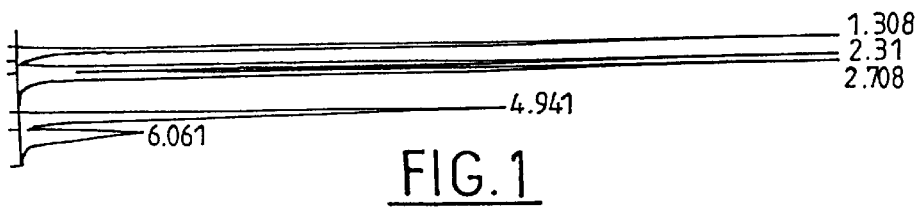
Figure 2:
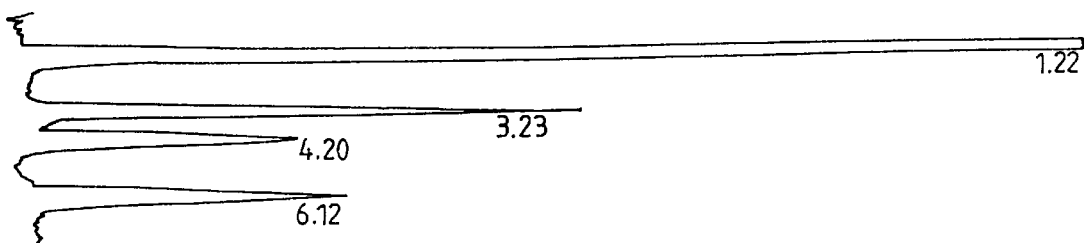
Figure 3:
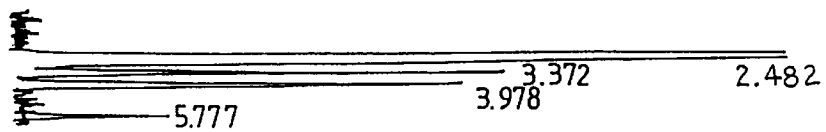
Figure 4A:
Figure 4B:
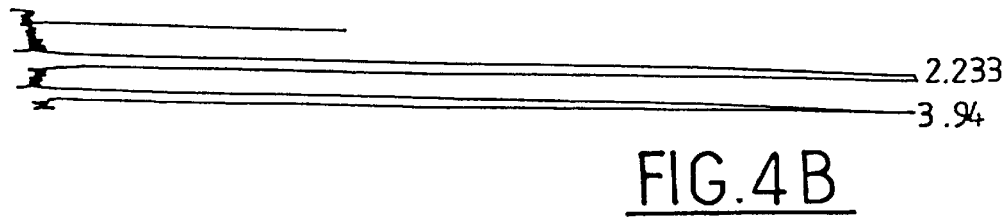
Figure 4C:
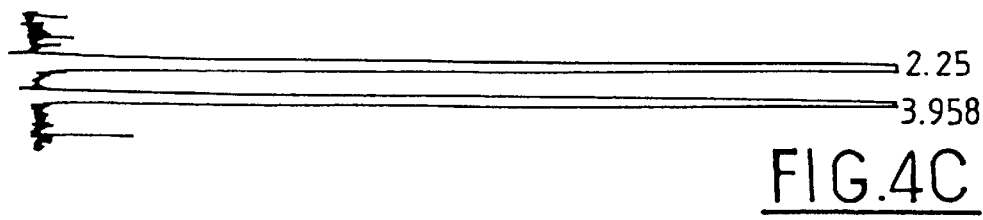
Figure 5A:
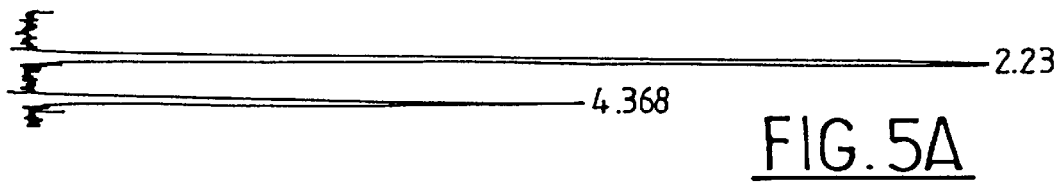
Figure 5B:
Figure 6A:
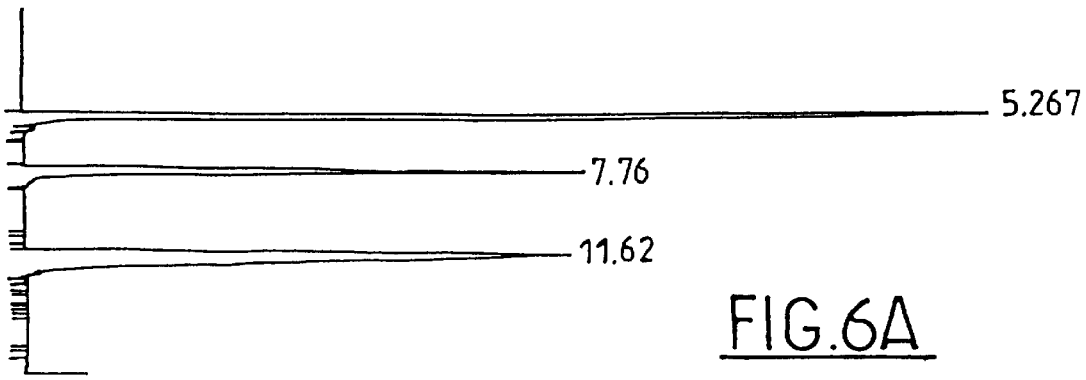
FIG. 6A represents the analysis of a mixture of NaCl and $MgCl_2$. The first peak corresponding to a retention time of 5.267 min. represents the $Cl^-$ ion whereas the subsequent two peaks, which correspond to retention times of 7.76 and 11.62 min. represent respectively the $Na^+$ and $Mg^{++}$ ions.
Figure 6B:
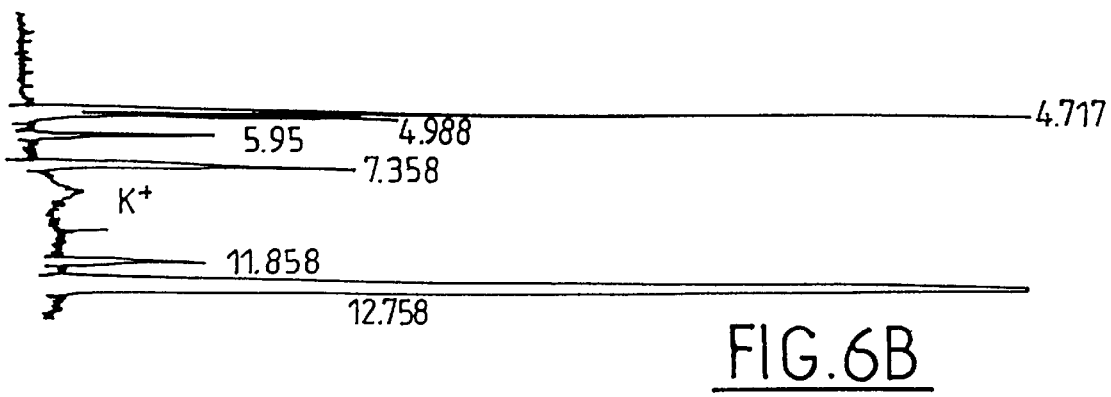
FIG. 6B represents the analysis of a mineral water (Perrier® water). The successive peaks, which correspond to retention times of 4.717; 4.988; 5.95; 7.358; 11.858 and 12.758 min., represent respectively the $Cl^-$; $SO_4^-$, $NO_3^-$, $Na^+$, $Mg^{++}$ and $Ca^{++}$ ions.
Figure 6C:
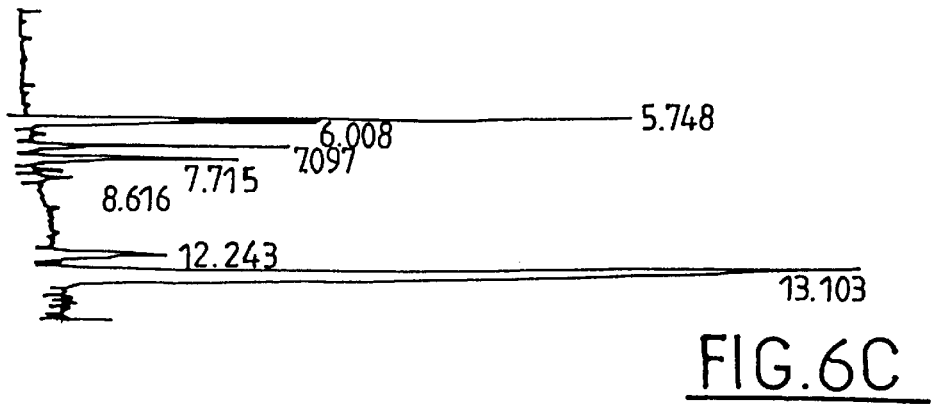

FIG. 6C represents the analysis of a domestic water. The successive peaks, which correspond to retention times of 5.748; 6.008; 7.097; 7.715; 8.616; 12.243 and 13.103 min., correspond respectively to the $Cl^-$, $SO_4^-$, $NO_3^-$, $Na^+$, $K^+$, $Mg^{++}$ and $Ca^{++}$ ions.

This example therefore demonstrates that the method proposed by the invention can be used to conduct an immediate and simultaneous analysis on anions and cations contained in a sample, the anions being eluted first, followed by the cations.

EXAMPLE 7

Simultaneous Analysis of Anions and Cations by Pairing Two Different Stationary Phases Using an Eluant of a Given Composition in Which the Concentration is Varied A mineral water (VOLVIC® water) is analysed on two stationary phases made up by combining a HYPERCARB® 7 μm column (4.6×100 mm) and a LICHROSIL® 5 μm column (4.6×100 mm), i.e. a strong cation exchanger.

After injecting in 75 microliters of the water sample to be analysed, different concentrations of a mobile phase comprising a solution containing 100 mM/1 of formic acid and 60 mM/1 of ammonia with a pH of 3.71 are fed through the different columns under the following conditions:

Flow rate=0.8 ml. $min^{-1}$; $T_D$=45° C.; $P_D$=2.1 bars; PM=10.

More specifically, after injecting in the sample to be analysed, this same mobile phase with a concentration of 25% was fed through the columns for 7 min. (i.e. between the times 0 and 7 min), followed, for the next 8 min. (i.e. between the times 7 and 15 min), by the above-mentioned phase again but with its concentration being 5 constantly varied between 25%. and 100% and finally, for the following 10 min. (i.e. between the times 15 and 25 min) the same mobile phase at a concentration of 100%.

The eluant was analysed on the ELSD at the output of the columns.

Figure 7:
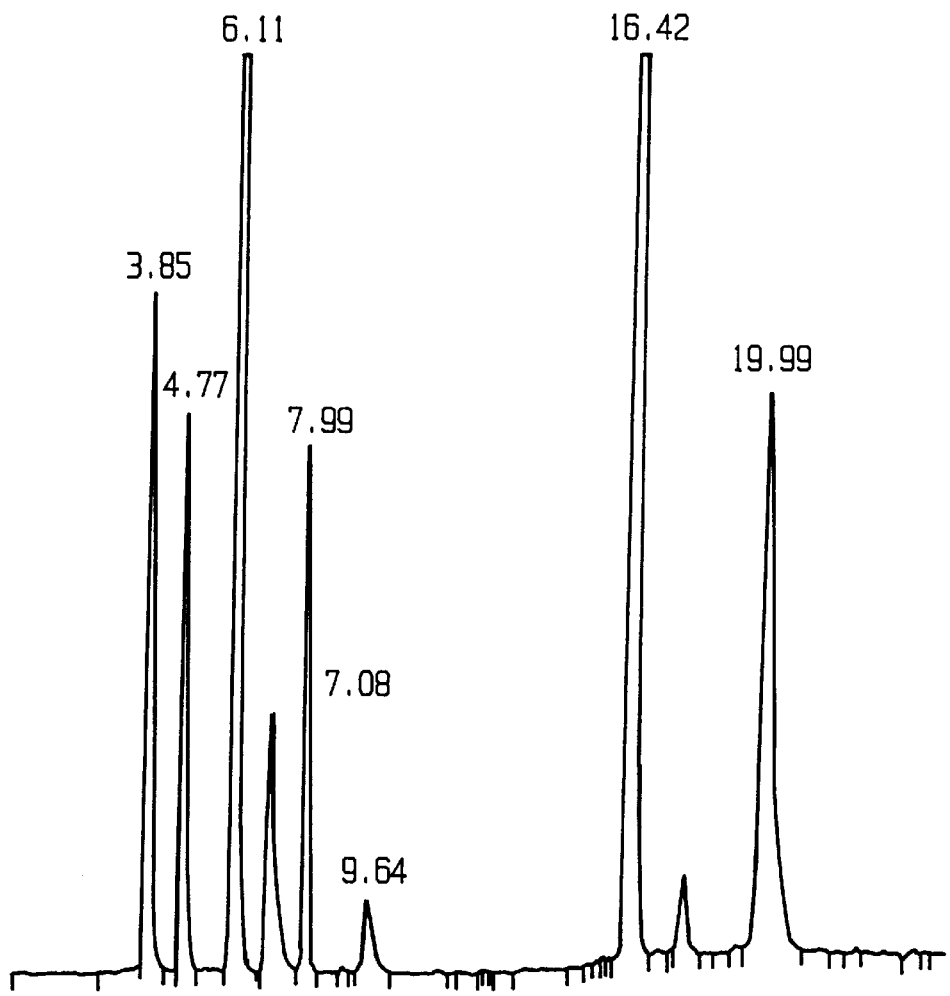

The chromatogram obtained is illustrated in FIG. 7. The successive peaks are set out in the table below.

| Retention time | Compound | Efficiency (Plate Number) | Width at mid-height (sec.) |
|---|---|---|---|
| 3.85 | not identified | | |
| 4.77 | Chloride | 5022 | 9.5 |
| 6.11 | Sodium | 9156 | 9.02 |
| 7.08 | Sulphate | 3806 | 16.2 |
| 7.99 | Potassium | 20130 | 16.4 |
| 9.64 | Nitrate | 6809 | 16.5 |
| 16.42 | Magnesium | 27242 | 14.1 |
| 19.99 | Calcium | 14559 | 23.4 |

This example therefore demonstrated that the method proposed by the invention can be used to elute the cations and anions simultaneously and in a selective manner, i.e. without any co-elution of the different species and, alternatively, for the first five eluates, namely $Cl^-$ then $Na^+$ then $SO_4^-$ then $K^+$ and finally $NO_3^-$.

The two examples 6 and 7 demonstrate that b) choosing correctly the two columns to be coupled, it will be possible to predict the order of elution between anions and cations and to do so without any co-elution of the different species.

With regard to the amounts of anions and cations in the water samples, it is sufficient to use standard curves such as can be set up using any detector.

What is claimed is:

1. A method of separating and analysing slightly volatile cations and anions contained in a sample immediately and simultaneously, characterised in that the sample is injected into a chromatography device in liquid phase co-operating with at least one stationary phase likely to retain the cations and the anions contained in the sample by competing interactions with the stationary phase or phases;

the cations and anions are eluted by feeding at least one mobile phase which can be evaporated through the stationary phase or phases; and the cations and anions present in this mobile phase or mobile phases are analysed immediately by means of an evaporative light scattering detector.

2. A method as claimed in claim 1, characterised in that the sample is fed through two columns coupled with one another, in particular set up in series, one of these columns retaining the cations whilst the other retains the anions, or through one column filled with two different stationary phases which may optionally be mixed, one of which retains the anions and the other retains the cations, or alternatively through a column filled with a single stationary phase which will retain the cations and the anions.

3. A method as claimed in claim 2, characterised in that the column which retains the cations and the column which retains the anions can be automatically switched.

4. A method as claimed in claim 1, characterised in that the stationary phase which retains the cations is a cation exchanger.

5. A method as claimed in claim 1, characterised in that the stationary phase which retains the anions is an anion exchanger.

6. A method as claimed in claim 1, characterised in that the stationary phase which retains the anions is porous graphitized carbon.

7. A method as claimed in claim 1, characterised in that the single stationary phase which retains the anions and the cations is a functionalised polymer.

8. A method as claimed in claim 1, characterised in that a mobile phase is fed through the one or two stationary phases to elute the cations or anions followed by a mobile phase to elute the anions or cations or, alternatively, a mobile phase to elute the cations and anions simultaneously and in a selective manner, i.e. without any co-elution of the different species.

9. A method as claimed in claim 8, characterised in that the mobile phase used to elute the cations and the mobile phase used to elute the anions consist of solutions of the same composition but having different concentrations.

10. A method as claimed in claim 9, characterised in that the mobile phases are aqueous solutions of formic acid and ammonia.

11. A method as claimed in claim 10, characterised in that after injecting the cations and anions to be analysed into the chromatography device, an aqueous solution of formic acid and ammonia in a low concentration is fed through the stationary phase or two stationary phases so that the cations remain locked whilst the anions are eluted, followed by an aqueous solution of formic acid and ammonia in a higher concentration in order to elute the cations.

12. A method as claimed in claim 8, characterised in that the mobile phase used to elute the cations and the mobile phase used to elute the anions are solutions of different compositions at identical or different concentrations.

13. A method as claimed in claim 1, characterised in that at least one stationary phase is inserted in the injection loop of the chromatography device in order to prepare a pre-concentration which may or may not be selective.

* * * * *